US008277820B2

(12) United States Patent
Ushijima et al.

(10) Patent No.: US 8,277,820 B2
(45) Date of Patent: Oct. 2, 2012

(54) PROCESS FOR PREPARING VARIANT OF *ERYSIPELOTHRIX RHUSIOPATHIAE* SURFACE PROTECTIVE ANTIGEN IN *E. COLI*

(75) Inventors: Toshihiro Ushijima, Kikuchi (JP); Masashi Sakaguchi, Kikuchi (JP); Eiji Tokunaga, Kikuchi (JP)

(73) Assignee: Juridical Foundation The Chemo-Sero-Therapeutic Research Institute, Kumamoto-Ken (JP)

( * ) Notice: Subject to any disclaimer, the term of this patent is extended or adjusted under 35 U.S.C. 154(b) by 710 days.

(21) Appl. No.: 10/590,896

(22) PCT Filed: Feb. 8, 2005

(86) PCT No.: PCT/JP2005/001814
§ 371 (c)(1),
(2), (4) Date: Aug. 28, 2006

(87) PCT Pub. No.: WO2005/083072
PCT Pub. Date: Sep. 9, 2005

(65) Prior Publication Data
US 2008/0286309 A1    Nov. 20, 2008

(30) Foreign Application Priority Data

Feb. 27, 2004  (JP) .................................. 2004-053882

(51) Int. Cl.
*A61K 39/00* (2006.01)
*A61K 39/38* (2006.01)
*A61K 39/02* (2006.01)
*C12P 21/06* (2006.01)
*C12N 15/09* (2006.01)

(52) U.S. Cl. ................... 424/234.1; 435/69.1; 435/69.3; 424/184.1; 424/185.1; 530/350

(58) Field of Classification Search ........................ None
See application file for complete search history.

(56) References Cited

FOREIGN PATENT DOCUMENTS

| JP | 06-030771 | 2/1994 |
| JP | 2000-279179 | 10/2000 |
| JP | 2002-034568 | 2/2002 |
| JP | 2002-306163 | 10/2002 |
| WO | WO 00/47744 | * 8/2000 |

OTHER PUBLICATIONS

Houghten et al. (New Approaches to Immunization, Vaccines 86, Cold Spring Harbor Laboratory, p. 21-25, 1986).*
Colman et al. (Research in Immunology 145: 33-36, 1994, p. 33 col. 2, p. 35 col. 1).*
Harlow et al., Antibodies a Laboratory Manual, Cold Spring Harbor Laboratory Press Inc., 1988, pp. 23-25, 27-33.*
Greenspan et al, Nature Biotechnology 17:936-937, 1999.*
Colman et al. (Research in Immunology 145: 33-36, 1994.*
Houghten et al. (New Approaches to Immunization, Vaccines 86, Cold Spring Harbor Laboratory, p. 21-25, 1986.*
Cloning and Expression in *Escherichia coli* of a Protective Antigen of *Erysipelothrix rhusiopathiae*, Jorge E. Galan, John F. Timoney Department of Veterinary Microbiology, New York State College of Veterinary Medicine, Cornell University, Ithaca New York 14853, vol. 58. No. 9, Sep. 1990, p. 3116-3121, Infection and Immunity.
Immunological Characterization of a Protective Antigen of *Erysipelothrix rhusiopathiae*: Identification of the Region Responsible for Protective Immunity, Yoshihiro Shimoji, Yasuyuki Mori, and Vincent A. Fischetti, Apr. 1999, p. 1646-1651, Laboratory of Bacterial Pathogenesis and Immunology, The Rockefeller University, New York New York 10021, and National Institute of Animal Health, Tsukuba, Ibaraki 305 Japan, Infection and Immunity.
Imada, Y. (1998):69 kDa Protective antigen of *Erysipelothrix rhusiopathiae*. Proc. Jpn. Pig Vet Soc. 34: 12-15.
Properties of repeat domain found in a novel protective antigen, SpaA, of *Erysipelothrix rhusiopathiae*, Sou-ichi Makino et al, 1998: 25: 101-109 Department of Veterinary Microbiology, University of Agriculture and Veterinary Medicine, Obihiro Hokkaido 080-8555, Japan, Microbia Pathogenesis, 1998 25:101-109.
Truncated Surface Protective Antigen (SpaA) of *Erysipelothrix rhusiopathiae* Serotype 1a Elicits Protection against challenge with Serotypes 1a and 2b in Pigs, Yumiko Imada et al., Sep. 1999, p. 4376-4382, vol. 67, No. 9, Infection and Immunity.
Y. Imada et al., "Enzyme-Linked Immunosorbent Assay Employing a Recombinant Antigen for Detection of Protective Antibody against Swine Erysipelas", Journal of Clinical Microbiology, vol. 41, No. 11, pp. 5015-5021, Nov. 2003.
M. Kesik et al., "Inclusion bodies from recombinant bacterial as a novel system for delivery of vaccine antigen by the oral route", Immunology Letters, vol. 91, pp. 197-204, 2004.
R. Kleemann et al., "Characterization of catalytic centre mutants of macrophage migration inhibitory factor (MIF) and comparison to Cys81Ser MIF", Eur. J. Biochem. vol. 261, pp. 753-766, 1999.
S. A. Krupenko et al., "On the Role of Conserved Histidine 106 in 10-Formyltetrahydrofolate Dehydrogenase Catalysis", Journal of Biological Chemistry, vol. 276, No. 26, pp. 24030-24037, Jun. 29, 2001. J. D. Phillips et al., "Functional consequences of naturally occurring mutations in human uroporphyrinogen decarboxylase", Blood, vol. 98, No. 12, pp. 3179-3185, Dec. 1, 2001.
U. Rinas et al., "Cysteine to serine substitutions in basic fibroblast growth factor: effect on inclusion body formation and proteolytic susceptibility during in vitro refolding", Bio/Technology, vol. 10, No. 4, pp. 435-440, 1992.
Supplementary European Search Report mailed Jul. 11, 2008, for EP 5709866.7/PCT/JP200500184.

* cited by examiner

*Primary Examiner* — Oluwatosin Ogunbiyi
(74) *Attorney, Agent, or Firm* — Browdy and Neimark, PLLC

(57) ABSTRACT

A variant of *Erysipelothrix rhusiopathiae* surface protective antigen SpaA protein or of a shortened form of SpaA (ΔSpaA) in which a portion of SpaA protein is deleted for protection from *Erysipelothrix rhusiopathiae* infection and a process for preparing the same are provided. Introduction of amino acid substitution at a specific site in the amino acid sequence of SpaA or ΔSpaA protein provides a variant of SpaA or ΔSpaA protein which is immunogenic and is expressed in *E. coli* as inclusion bodies. The variant of SpaA or ΔSpaA protein of the present invention may easily be recovered and purified since it is expressed in *E. coli* as inclusion bodies.

13 Claims, 6 Drawing Sheets

PROCESS FOR PREPARING VARIANT OF ERYSIPELOTHRIX RHUSIOPATHIAE SURFACE PROTECTIVE ANTIGEN IN E. COLI

TECHNICAL FIELD

The present invention relates to a process for preparing a variant of *Erysipelothrix rhusiopathiae* surface protective antigen (hereinafter also referred to as "SpaA") with *Escherichia coli* as a host. More particularly, the present invention relates to a process for preparing a variant of SpaA or of a shortened form of SpaA (hereinafter also referred to as "ΔSpaA"), in which a portion of SpaA is deleted, with introduction of amino acid substitution wherein said variant may be expressed as insoluble inclusion bodies when expressed within the cells of *E. coli*, and to a variant of a recombinant SpaA or ΔSpaA protein obtained by said process.

BACKGROUND ART

Porcine erysipelas is a swine disease caused by infection with *Erysipelothrix rhusiopathiae* wherein infected swine suffers from symptoms such as sepsis in acute cases, hives in subacute cases, or endocarditis and arthritis in chronic cases. Around 3,000 swine per year have been reported to have the disease which is a great deal of damage to a stockbreeder. *Erysipelothrix rhusiopathiae* is pathogenic either to food animals such as wild boar, whales, chickens and turkeys in addition to swine and is specified as one of supervisory infectious diseases in the Protective Act of Livestock Diseases. Porcine erysipelas is also zoonosis that causes erysipeloid in human and is of importance in view of meat hygiene. There are a number of serotypes in *Erysipelothrix rhusiopathiae*, among which serotypes 1 and 2 cause most of porcine erysipelas in swine.

For protection of porcine erysipelas infections, there have hitherto been used attenuated live vaccines, i.e. freeze-dried live vaccines prepared by using Koganei strain which is an attenuated strain of *Erysipelothrix rhusiopathiae* prepared by subculturing virulent *Erysipelothrix rhusiopathiae* in a medium supplemented with acriflavine for a long period; inactivated vaccines, i.e. bacteria vaccines prepared by treating a culture of virulent *Erysipelothrix rhusiopathiae* with formalin and rendering the whole cells and extracellular products be adsorbed to aluminum hydroxide gel; and component vaccines, i.e. ones comprising a fraction of non-purified surface proteins of the cells extracted from the whole cells with an aqueous alkali solution. Attenuated live vaccines are thought to be much less costly since they may be efficacious with only one administration in a small amount. However, it is indicated they are also problematic in that they are pathogenic in mice to induce arthritis, that they exhibit severe side effects in swine with a low antibody level or SPF swine, and that the vaccine strain is isolated from the lesion of swine suffering from porcine erysipelas.

As a new type of vaccines, research and development is on-going for recombinant vaccines by the use of genetic recombination technique. Galan and Timony immunized mice with a lysate of *E. coli* transfected with a recombinant phage expressing genes from a part of *Erysipelothrix rhusiopathiae* genome and performed a challenge test with *Erysipelothrix rhusiopathiae* to observe that 14 to 17% of the immunized mice escaped from death after infection. Furthermore, they revealed that the proteins encoded by the genes are ones having molecular weight 66, 64, and 43 kDa from their reactivity with an immune serum against the lysate and demonstrated that these proteins could be protective antigens to *Erysipelothrix rhusiopathiae* infection (see e.g. Non-patent reference 1).

Makino et al. expressed a gene coding for a surface protein of a molecular weight 64 kDa (named "SpaA") from type 2 *Erysipelothrix rhusiopathiae* Tama 96 strain in *E. coli*, immunized mice with live cells of the resulting recombinant *E. coli*, and performed a challenge test with *Erysipelothrix rhusiopathiae* to demonstrate that SpaA protein had protective activity to infection. They also revealed that SpaA protein had a sequence of 606 amino acid residues wherein a signal peptide consisting of 29 amino acids is at its N-terminal and eight homologous sequences of repeat, each repeat consisting of 20 amino acids excepting the 8th repeat which consists of 19 amino acids, are at its C-terminal (see e.g. Non-patent reference 2).

Imada et al. investigated SpaA protein from type 1 Fujisawa strain corresponding to the above SpaA protein and a gene encoding said protein to reveal that SpaA protein from type 1 Fujisawa strain is one with a molecular weight 69 kDa that has a sequence of 626 amino acid residues with one more, i.e. nine, homologous sequences of repeat at its C-terminal, as compared to the type 2 SpaA protein, with the 9th repeat consisting of 19 amino acids. They demonstrated that a fusion protein of a full-length SpaA, SpaA with deletion of the homologous sequences of repeat at the C-terminal, or SpaA with deletion of a portion of the N-terminal and the homologous sequences of repeat at the C-terminal, with a histidine hexamer, exhibited a protective effect to infection (see e.g. Non-patent references 3 and 4).

Watanabe et al. also reported that a polypeptide of 46.5 kDa prepared by deleting the homologous sequences of repeat at the C-terminal and a secretion signal sequence at the N-terminal from *Erysipelothrix rhusiopathiae* SpaA protein could be a protective antigen to infection (46.5 kDa protective antigen; named "46.5 KPA")(see e.g. Patent reference 1).

On the other hand, promotion of productivity of a candidate protein for vaccine has been attempted. For instance, there is a report that 46.5 KPA could successfully be expressed for secretion out of the cells using *Brevibacillus choshinensis* as a host cell (see e.g. Patent reference 2). With this expression system, about 50% of an expressed protein becomes insoluble due to coagulation in culture. According to the report, purification of said insolubilized 46.5 KPA was performed by filtering a culture with ultrafiltration membrane, suspending the insoluble materials recovered on the membrane in an alkaline solution, and recovering the solubilized 46.5 KPA. Thus, this purification process requires at least three steps: (1) condensation through ultrafiltration under neutral to weak alkaline condition (pH 7 to 9.5); (2) recovery of a filtration fraction through ultrafiltration under strong alkaline condition (pH 10.0 to 12.0); and (3) purification of the ultrafiltration fraction by ion exchange chromatography.

When SpaA gene is expressed in *E. coli*, most of the protein may be expressed as a soluble protein and hence the purification process for insoluble materials as described above may not be applied. A culture may contain, other than SpaA protein of interest, various contaminants such as cell debris of *E. coli*, components from a culture medium, metabolic products produced while culture, etc. It is not easy to efficiently recover and purify the soluble SpaA protein of interest from such admixtures of contaminants. In general, a vaccine for animals, unlike a vaccine for human, would not be accepted by a stockbreeder unless it is low priced as well as in high purity and high quality. Accordingly, a manufacturer of a vaccine for animals is always required for improvement in a process for production and a process for recovery and purification that enables treatment in large scale and reduction of cost for production.

Patent reference 1: Japanese patent publication No. 2000-279179

Patent reference 2: Japanese patent publication No. 2002-34568

Non-patent reference 1: Garan, J. E. et al., (1990) Infect. Immun., 58. p. 3116-3121

Non-patent reference 2: Makino, S. et al., (1998) Microb. Pathog. 25, p. 101-109

Non-patent reference 3: Imada, Y. et al. (1999) Proc. Jpn. Pig. Vet. Soc. 34, p. 12-

Non-patent reference 4: Imada, Y. et al. (1999) Infect. Immun. 67 (9), p. 4376-4382

DISCLOSURE OF THE INVENTION

Technical Problem to be Solved by the Invention

As described above, when SpaA gene from *Erysipelothrix rhusiopathiae* is expressed in *E. coli* or *Brevibacillus choshinensis* as a host, the protein is expressed as a soluble SpaA protein or in admixture of the soluble and insoluble proteins, which renders process for its production troublesome and does not allow for expectation of high yield.

The present invention has been accomplished in view of necessity on the technical or industrial background as described above. Thus, an object of the present invention is to provide a process for preparing SpaA or a shortened form of SpaA (ΔSpaA) in which a portion of SpaA is deleted, which comprises introducing amino acid substitution in the amino acid sequence of SpaA or ΔSpaA protein so that intrinsically soluble SpaA or ΔSpaA protein could be expressed as inclusion bodies within the cells of *E. coli*, and recovering and purifying the inclusion bodies.

Another object of the present invention is to provide a recombinant SpaA or ΔSpaA protein obtained by said process in high purity.

Means for Solving the Problems

The present inventors have continued research assiduously so as to attain the objects as described above and as a consequence have found that there existed clones that may form insoluble inclusion bodies among *E. coli* cells in which SpaA or ΔSpaA protein is expressed, that amino acid substitution occurred at a specific site in the amino acid sequence of SpaA or ΔSpaA protein that formed inclusion bodies, and that artificial introduction of said amino acid substitution may allow for accumulation of soluble SpaA or ΔSpaA protein as inclusion bodies within the cells. Furthermore, the present inventors have found that soluble SpaA or ΔSpaA protein retained immunogenicity even after formation of inclusion bodies to thereby complete the present invention. By way of example, inclusion bodies may be formed when the 69th amino acid in SpaA or ΔSpaA protein from SE-9 strain is substituted with glycine; the 214th amino acid is substituted with glutamine; the 278th amino acid is substituted with glycine; the 531st amino acid is substituted with glycine; the 154th and 203rd amino acids are substituted with glycine and threonine, respectively; the 214th and 253rd amino acids are substituted with glutamine and threonine, respectively; or the 69th, 154th and 203rd amino acids are substituted with glycine, glycine and threonine, respectively.

The present invention generally provides a process for preparing a variant of *Erysipelothrix rhusiopathiae* surface protective antigen SpaA protein or of a shortened form of SpaA (ΔSpaA) in which a portion of SpaA protein is deleted, said variant having immunogenicity and being expressed in *E. coli* as inclusion bodies, which comprises mutating a gene coding for said SpaA or ΔSpaA protein so that amino acid substitution may be introduced in the amino acid sequence of said SpaA or ΔSpaA protein, allowing the resulting mutated gene to be expressed in *E. coli*, and selecting such variants that formed inclusion bodies among the variants expressed. Thus, the process according to the present invention is characterized by that SpaA or ΔSpaA protein, of which intrinsically soluble property has made recovery and purification of said protein difficult, may be expressed in *E. coli* as insoluble inclusion bodies by preparing a variant of SpaA or ΔSpaA protein through amino acid substitution that enables expression of said protein as insoluble inclusion bodies to thereby facilitate recovery and purification of said protein.

In one embodiment, the process of the present invention comprises the following steps (A) to (D):

(A) introducing mutation in a gene coding for soluble *Erysipelothrix rhusiopathiae* surface protective antigen SpaA or ΔSpaA protein so that amino acid substitution may be introduced;

(B) transforming *E. coli* cells with an expression vector containing the resulting mutated gene;

(C) selecting *E. coli* cells that formed insoluble inclusion bodies among the above transformed *E. coli* cells; and (D) culturing the selected *E. coli* cells for recovery of the inclusion bodies within the cells.

To confirm that a variant of recombinant SpaA or ΔSpaA protein obtained by the process of the present invention retains a protective activity (immunogenicity) to *Erysipelothrix rhusiopathiae* infection, the variant may be further subject to the following steps (E) to (F):

(E) administering the inclusion bodies or the inclusion bodies treated with a solubilizing agent to an animal sensitive to *Erysipelothrix rhusiopathiae* infection and then attacking said animal with a virulent strain of *Erysipelothrix rhusiopathiae*; and (F) observing survival or death of the animal sensitive to *Erysipelothrix rhusiopathiae* to thereby assess the presence of a protective activity (immunogenicity) against *Erysipelothrix rhusiopathiae* infection.

The process of the present invention is characterized by that SpaA or ΔSpaA protein, which is intrinsically soluble, may be converted into its variant that may be expressed in *E. coli* as insoluble inclusion bodies to thereby facilitate recovery and purification of said protein. In accordance with the process of the present invention, for expression of SpaA or ΔSpaA protein as insoluble inclusion bodies, a gene coding for SpaA or ΔSpaA protein is mutated to introduce amino acid substitution in the amino acid sequence of said SpaA or ΔSpaA protein. Among the thus prepared variants of SpaA or ΔSpaA protein with amino acid substitution are included those that may be expressed by forming inclusion bodies, which are then selected. Accordingly, mutation introduced in a gene coding for SpaA or ΔSpaA protein or amino acid substitution caused in the amino acid sequence of said SpaA or ΔSpaA protein may be any mutation or amino acid substitution so far as it results in a variant of SpaA or ΔSpaA protein that may be expressed by forming inclusion bodies.

An example of such amino acid substitution includes one or a combination of more than one selected from the group consisting of (1) to (7) as described below:

(1) the 69th amino acid from the N-terminal encompassing the signal sequence is substituted with glycine;

(2) the 154th amino acid from the N-terminal encompassing the signal sequence is substituted with glycine;

(3) the 203rd amino acid from the N-terminal encompassing the signal sequence is substituted with threonine;

(4) the 214th amino acid from the N-terminal encompassing the signal sequence is substituted with glutamine;

(5) the 253rd amino acid from the N-terminal encompassing the signal sequence is substituted with threonine;

(6) the 278th amino acid from the N-terminal encompassing the signal sequence is substituted with glycine; and (7) the 531st amino acid from the N-terminal encompassing the signal sequence is substituted with glycine.

Another example of such amino acid substitution includes: the 154th and 203rd amino acids from the N-terminal encompassing the signal sequence are substituted with glycine and threonine, respectively; the 214th and 253rd amino acids from the N-terminal encompassing the signal sequence are substituted with glutamine and threonine, respectively; and the 69th, 154th and 203rd amino acids from the N-terminal encompassing the signal sequence are substituted with glycine, glycine and threonine, respectively.

The amino acid sequence of SpaA or ΔSpaA protein may be the sequence as depicted in SEQ ID NO: 2 or the sequence as depicted in SEQ ID NO: 2 with deletion at its C-terminal wherein a desired amino acid substitution, in particular, those as described above, may be introduced.

In another embodiment, the present invention provides a variant of *Erysipelothrix rhusiopathiae* surface protective antigen SpaA or ΔSpaA protein which is immunogenic and expressed in *E. coli* as inclusion bodies. The variant of SpaA or ΔSpaA protein of the present invention is preferably prepared by the process as described herein. The term "a variant of *Erysipelothrix rhusiopathiae* surface protective antigen SpaA or ΔSpaA protein" as used herein refers to an insoluble protein mutated from a soluble *Erysipelothrix rhusiopathiae* surface protective antigen SpaA or ΔSpaA protein by specific amino acid substitution. The term "immunogenicity" or "immunogenic" means a capacity of inducing production of a protective antibody or a capacity of protecting from *Erysipelothrix rhusiopathiae* infection.

Yet in another embodiment, the present invention provides a composition comprising as an active ingredient a variant of *Erysipelothrix rhusiopathiae* surface protective antigen SpaA or ΔSpaA protein of the present invention. The variant of SpaA or ΔSpaA protein of the present invention contained in said composition is preferably prepared by the process as described herein.

In yet another embodiment, the present invention provides a gene coding for a variant of *Erysipelothrix rhusiopathiae* surface protective antigen SpaA or ΔSpaA protein which is immunogenic and expressed in *E. coli* as inclusion bodies. The gene coding for a variant of SpaA or ΔSpaA protein of the present invention is preferably prepared by the process as described herein. The gene coding for a variant of SpaA or ΔSpaA protein of the present invention includes at least one nucleotide substitution as compared to a gene coding for SpaA or ΔSpaA protein. Said at least one nucleotide substitution however should not be a silent mutation but must induce at least one amino acid substitution (point mutation) in SpaA or ΔSpaA protein.

An example of a gene coding for a variant of SpaA or ΔSpaA protein of the present invention includes, for instance, a nucleotide sequence or a nucleotide sequence with deletion of a portion of the 3'-terminal, which includes one or a combination of more than one nucleotide substitution in SEQ ID NO: 1 selected from the group consisting of (1) to (7) as described below:

(1) the 206th nucleotide in the nucleotide sequence as depicted in SEQ ID NO: 1 is G;

(2) the 461st nucleotide in the nucleotide sequence as depicted in SEQ ID NO: 1 is G;

(3) the 608th nucleotide in the nucleotide sequence as depicted in SEQ ID NO: 1 is C;

(4) the 642nd nucleotide in the nucleotide sequence as depicted in SEQ ID NO: 1 is G;

(5) the 758th nucleotide in the nucleotide sequence as depicted in SEQ ID NO: 1 is C;

(6) the 833rd nucleotide in the nucleotide sequence as depicted in SEQ ID NO: 1 is G; and (7) the 1591st nucleotide in the nucleotide sequence as depicted in SEQ ID NO: 1 is G.

Another example of a gene coding for a variant of SpaA or ΔSpaA protein of the present invention includes, for instance, a nucleotide sequence or a nucleotide sequence with deletion of a portion of the 3'-terminal, which includes any of nucleotide substitution in SEQ ID NO: 1 selected from the group consisting of (a) to (h) as described below:

(a) the 206th nucleotide in the nucleotide sequence as depicted in SEQ ID NO: 1 is G;

(b) the 608th nucleotide in the nucleotide sequence as depicted in SEQ ID NO: 1 is C;

(c) the 642nd nucleotide in the nucleotide sequence as depicted in SEQ ID NO: 1 is G;

(d) the 833rd nucleotide in the nucleotide sequence as depicted in SEQ ID NO: 1 is G; and (e) the 1591st nucleotide in the nucleotide sequence as depicted in SEQ ID NO: 1 is G;

(f) the 461st and 608th nucleotides in the nucleotide sequence as depicted in SEQ ID NO: 1 are G and C, respectively;

(g) the 642nd and 758th nucleotides in the nucleotide sequence as depicted in SEQ ID NO: 1 are G and C, respectively; and (h) the 206th, 461st and 608th nucleotides in the nucleotide sequence as depicted in SEQ ID NO: 1 are G, G and C, respectively.

In still another embodiment, the present invention provides a method for using a variant of *Erysipelothrix rhusiopathiae* surface protective antigen SpaA or ΔSpaA protein of the present invention as a vaccine for porcine erysipelas. The variant of SpaA or ΔSpaA protein of the present invention used in said method is preferably prepared by the process as described herein.

*Erysipelothrix rhusiopathiae* for use in preparing a variant of *Erysipelothrix rhusiopathiae* surface protective antigen SpaA or ΔSpaA protein of the present invention includes, for instance, Fujisawa strain, Koganai strain for type 1, and Tama 96 strain, SE-9 strain or Shizuoka 63 strain for type 2 but SpaA gene from any strain of *Erysipelothrix rhusiopathiae* may be used in the present invention.

More Efficacious Effects than Prior Art

In accordance with the present invention, a method for expressing soluble SpaA or ΔSpaA protein in *E. coli* as insoluble inclusion bodies is provided. The expression in *E. coli* as inclusion bodies allows for purification of SpaA or ΔSpaA protein easily in high purity simply by centrifugation and washing procedures. The thus obtained inclusion bodies of SpaA or ΔSpaA protein, after solubilization, have sufficient purity and immunogenicity for use as a vaccine only if diluted. Thus, a simple and efficient method for preparing a SpaA or ΔSpaA protein vaccine is provided. With the use of SpaA or ΔSpaA protein obtained by said method, opportunity of *Erysipelothrix rhusiopathiae* infection to human may be reduced as compared to a method for preparing an inactivated vaccine or a component vaccine which employs *Erysipelothrix rhusiopathiae* as a starting material. The present invention also evades problems of restoration of pathogenicity in *Erysipelothrix rhusiopathiae*, severe side effects found in swine with low antibody titer or SPF swine, and the like.

BEST MODE FOR CARRYING OUT THE INVENTION

Figure 1:
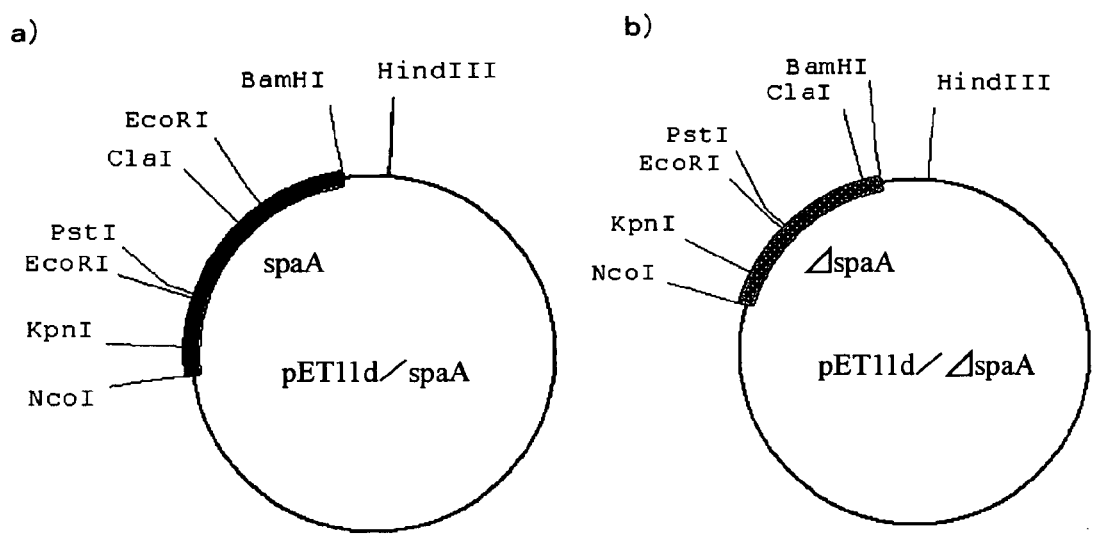
FIG. 1 shows an expression vector for SpaA or ΔSpaA protein. a: Plasmid pET11d/SpaA in which a gene coding for SpaA protein derived from *Erysipelothrix rhusiopathiae* SE-9 strain is inserted; b: Plasmid pET11d/ΔSpaA in which a gene coding for ΔSpaA protein is inserted.

The present invention is characterized by a method for expressing SpaA or ΔSpaA protein in *E. coli* as inclusion bodies by substituting an amino acid residue at a specific site in the amino acid sequence of said protein with a specific amino acid, and a process for preparing SpaA or ΔSpaA protein by incorporating said method.

(1) Cloning of a Gene Coding for SpaA or ΔSpaA Protein

For *Erysipelothrix rhusiopathiae*, there are chiefly two serotypes as exhibiting strong pathogenicity to swine which are classified into types 1 and 2. Type 1 includes Fujisawa strain and Koganai strain, whereas type 2 includes Tama 96 strain, SE-9 strain and Shizuoka 63 strain. However, a SpaA gene from any strain of *Erysipelothrix rhusiopathiae* may be used in the present invention. These cells may be grown with a commercially available culture medium in accordance with the instructions attached thereto. For instance, a fixed amount of the cells may be suspended in Brain Heart Infusion Broth supplemented with 0.1% Tween 80 and the suspension incubated at 37° C. for 16 to 48 hours.

A gene coding for SpaA or ΔSpaA protein may be obtained by PCR with DNAs extracted from the cells as described above as a template using primers designed from the sequence (SEQ ID NO: 1) described by Imada, Y. et al. (1999) Infect. Immun. 67 (9), p. 4376-4382. SEQ ID NO: 1 depicts a full-length nucleotide sequence of SpaA gene derived from Fujisawa strain whereas SEQ ID NO: 2 depicts an amino acid sequence of a full-length SpaA protein derived from Fujisawa strain encompassing a signal peptide. SEQ ID NO: 7 depicts a portion of a full-length nucleotide sequence of SpaA gene derived from SE-9 strain, which corresponds to the sequence of from the 107th to 1854th nucleotide residues in SEQ ID NO: 1. A template DNA may be prepared with a commercially available DNA extraction kit, e.g. Isoplant (NIPPON GENE CO., LTD.), in accordance with the instructions attached thereto. PCR primers are readily available from DNA synthesis contractor services, e.g. QIAGEN, by request, and are preferably added with a sequence of an appropriate restriction enzyme cleavage site at the 5' end. Specifically, synthetic DNAs may be used wherein NcoI site is added to SEQ ID NO: 2 or BamHI site is added to SEQ ID NO: 4 or SEQ ID NO: 5. Primers as depicted in SEQ ID NO: 3 and SEQ ID NO: 5 may be used for amplification of a DNA fragment coding for SpaA protein whereas primers as depicted in SEQ ID NO: 3 and SEQ ID NO: 4 may be used for amplification of a DNA fragment coding for ΔSpaA protein. The resulting DNA fragment coding for SpaA or ΔSpaA protein will have addition of twelve nucleotides coding for Met derived from the restriction enzyme NcoI and the three amino acids at the C-terminal (Ala-Phe-Ala). A DNA fragment coding for ΔSpaA protein has a partial SpaA gene up till the 1260th nucleotide and codes for a shortened form of SpaA protein with deletion of 207 amino acid residues at the C-terminal. Size and site of ΔSpaA protein where a portion of SpaA protein is deleted may be determined arbitrarily as occasion demands by altering a position of primer sequences. PCR reaction may be performed with a commercially available LA-Taq kit (TAKARA SHUZO CO.), Advantage HF-2 PCR Kit (BC Bioscience), etc. in accordance with the protocols attached thereto. A nucleotide sequence of the DNA fragments obtained by PCR may be determined with a DNA sequencer, e.g. ABI PRISM310 Genetic Analyzer (PE Biosystems), after cloning into a TA cloning kit (Invitrogen).

The thus obtained gene coding for SpaA or ΔSpaA protein is cloned. Specifically, the PCR products as described above are digested with the restriction enzymes NcoI and BamHI, the cleaved fragments are inserted into a suitable plasmid, e.g. pET11d (Novagen), which has previously been digested with the same restriction enzymes, and the resulting plasmid is introduced into *E. coli*. Among the colonies of *E. coli*, those clones having DNAs coding for the desired protein are selected. For a host E. coli, HB101, JM109, LE392, TB1, BL21 and the like may be used, preferably JM109. A method for introduction of a gene includes electroporation, protoplast, PEG, etc. and any of these techniques may be used. Cloning of a desired gene may be confirmed by purification of the plasmid and determination of the nucleotide sequence. A series of these procedures for genetic recombination may be performed in accordance with a general technique for genetic recombination as described by Sambrook et al., Molecular Cloning, A Laboratory Manual Second Edition, Cold Spring Harbor Laboratory Press, N.Y., 1989. In practice, it may be performed with a commercially available kit in accordance with the instructions attached thereto.

(2) Expression and Purification of Insoluble SpaA or ΔSpaA Protein

By making a point mutation at a specific site in the cloned gene coding for SpaA or ΔSpaA protein and introducing the resulting gene into E. coli, an intrinsically soluble SpaA or ΔSpaA protein can be expressed as insoluble inclusion bodies.

Point mutation may be performed by site-directed mutagenesis. In practice, a commercially available kit may be used, including Site-Directed Mutagenesis System from Takara (Mutan-Super Express Km, Mutan-Express Km, Mutan-K, etc.), QuickChange Multi Site-Directed Mutagenesis Kit or QuickChange XL Site-Directed Mutagenesis Kit from Stratagene, or GeneTailor Site-Directed Mutagenesis System from Invitrogen, in accordance with the instructions attached thereto. Point mutation may also be produced by replacing a nucleic acid fragment of a suitable size in which point mutation has been introduced.

Alternatively, as nucleotide substitution of unspecified numbers at unspecified sites may occur in amplified genes at some rate when normal PCR is performed, this may be utilized for introduction of nucleotide substitution. If substituted nucleotides affect amino acid codons, amino acid mutation may occur, thus possibility of occurrence of clones that form inclusion bodies. By selecting these clones, the inclusion bodies may be obtained.

A soluble SpaA or ΔSpaA protein is expressed in E. coli as insoluble inclusion bodies by e.g. substitution of the 69th amino acid from the N-terminal encompassing the signal sequence with glycine; substitution of the 154th amino acid with glycine; substitution of the 203rd amino acid with threonine; substitution of the 214th amino acid with glutamine; substitution of the 253rd amino acid with threonine; the 278th amino acid with glycine; and/or substitution of the 531st amino acid with glycine. Thus, point mutation in SpaA gene is performed so that these amino acid substitutions may occur. Inclusion bodies are formed by introducing amino acid mutation at least one of the sites described above but it is possible that amino acid mutation is introduced at all of these sites insofar as the resulting mutants remain immunogenic. Preferably, point mutation in SpaA gene is performed so that the 69th amino acid of SpaA or ΔSpaA protein is substituted with glycine; the 214th amino acid is substituted with glutamine; the 278th amino acid is substituted with glycine; the 531st amino acid is substituted with glycine; the 154th and 203rd amino acids are substituted with glycine and threonine, respectively; the 214th and 253rd amino acids are substituted with glutamine and threonine, respectively; or the 69th, 154th and 203rd amino acids are substituted with glycine, glycine and threonine, respectively.

A region and size of ΔSpaA protein, obtained by deletion of a portion of SpaA protein, is not subject to restriction insofar as ΔSpaA protein remains immunogenic and, when amino acid substitution is introduced, is capable of forming inclusion bodies. ΔSpaA protein wherein at least about ⅓ of the C-terminal of SpaA protein is deleted may be used in the present invention. Preferably, ΔSpaA protein comprises 420 amino acid residues from the N-terminal encompassing the signal sequence with deletion of 207 amino acids at the C-terminal.

Alternatively, it is also possible to conversely transform insoluble SpaA or ΔSpaA protein into soluble SpaA or ΔSpaA protein by introducing amino acid substitution in a converse manner to those described above. Thus, in accordance with the process of the present invention, either protein of soluble or insoluble SpaA or ΔSpaA may unrestrictedly be obtained as occasion demands.

Expression of the gene coding for SpaA or ΔSpaA protein in which point mutation is performed may be done as described above for cloning of the gene. An expression vector may be commercially available ones and appropriate E. coli is selected as a host. For instance, BL21(DE3) or DH5α(DE3) for a vector with a T7 promoter; HB101, DH5α or JM109 for a vector with a tryptophan promoter may be used. Preferably, a combination of pET11d (Novagen) vector, which allows for concomitant cloning and expression of a desired protein, with E. coli BL21 strain may be used.

Recombinant E. coli expressing SpaA or ΔSpaA protein may be screened as described below. In the presence of an expression inducer (in case of expression system as used in the present invention, IPTG is utilized), the cells cultured and grown are collected by centrifugation at low speed and suspended in an amount of distilled water. The cells are disrupted by sonication or with a homogenizer such as French Press, Manton Galling and are centrifuged at high speed (15,000 rpm, 15 minutes) to recover inclusion bodies in precipitates. Distilled water may appropriately be added with a surfactant (e.g. Triton X100), a chelating agent (e.g. EDTA), lysozyme, etc. Again, the precipitate is suspended in a suitable amount of distilled water and an amount of the suspension is applied to SDS-polyacrylamide gel electrophoresis. After staining with Coomassie Brilliant Blue, expression of SpaA or ΔSpaA protein is confirmed by molecular size and stained image. An amount of the formed inclusion bodies may be determined by comparing amounts of SpaA or ΔSpaA protein in supernatant and in precipitates after centrifugation as described above. In accordance with the present invention, about 90% or more of SpaA or ΔSpaA protein may be found in precipitates. For confirmation (or detection) of SpaA or ΔSpaA protein, procedures based on an antigen-antibody reaction such as ELISA, Western blot, dot blot, and the like may also be used in addition to one based on molecular size. These have been commonly used for detection of a foreign protein expressed in E. coli and any of these may suitably be selected as occasion demands.

For purification of SpaA or ΔSpaA protein from the thus obtained E. coli cells expressing SpaA or ΔSpaA protein, the method as described in Japanese patent publication No. 2002-34568 or purification procedures commonly used in protein chemistry such as e.g. centrifugation, salting-out, ultrafiltration, isoelectric precipitation, electrophoresis, ion exchange chromatography, affinity chromatography, hydrophobic chromatography, hydroxyapatite chromatography, or a combination thereof may be used. In accordance with the process of the present invention, 90% or more purity of SpaA or ΔSpaA protein may be achieved by treating a culture of E. coli cells expressing SpaA or ΔSpaA protein with either or both of an enzyme (e.g. lysozyme) and/or sonication (e.g. sound beam type cell homogenizer), followed by repetition of centrifugation (e.g. 15,000 rpm, 15 minutes) and suspension in a washing buffer (e.g. 20 mM Tris-HCl pH 7.5, 10 mM EDTA, 1% Triton X-100)

(3) Immunogenicity of SpaA or ΔSpaA Protein

Immunogenicity of the thus obtained SpaA or ΔSpaA protein may be determined by immunizing mice or other animals, infected with *Erysipelothrix rhusiopathiae*, with these proteins and challenging the animals with a virulent strain of *Erysipelothrix rhusiopathiae*. A mode of immunization, e.g. administration route such as subcutaneous, intramuscular or intraperitoneal, term of immunization, etc., may also be determined as commonly used for investigating immunogenicity of a vaccine. More specifically, the antigenic protein is serially diluted by 5-fold in saline supplemented with 25% (vol/vol) aluminum hydroxide gel to prepare serial dilution which is used for immunization of 5 to 10 mice (ddy, 5 weeks old, female) per dilution by subcutaneous administration. Three weeks after immunization, mice receive intradermal injection of live cells of Fujisawa strain, a virulent strain of *Erysipelothrix rhusiopathiae*, and survival or death of mice is observed for 10 days. Immunizing effects of the antigenic protein may be assessed by a median protective dose (PD50).

SpaA or ΔSpaA protein of the present invention, after purification in an insoluble form, may be solubilized with a solubilizing agent such as urea, guanidine hydrochloride or arginine hydrochloride, subjected to sterile filtration with a membrane filter etc., and used as materials for preparing a vaccine for protection of sensitive animals such as e.g. wild boar, whales, chickens, turkeys and human from infection with *Erysipelothrix rhusiopathiae* or other pathogens. The thus prepared SpaA or ΔSpaA protein may be formulated into a pharmaceutical composition by appropriately admixing it with an immunological adjuvant such as aluminum hydroxide, aluminum phosphate, mineral oil or non-mineral oil, a stabilizing agent such as Polysorbate 80, an amino acid or sugars such as lactose or sucrose, and a preserving agent such as formalin, thimerosal, 2-phenoxyethanol, benzyl alcohol, benzethonium chloride or benzalkonium chloride. When sugars such as lactose or sucrose effective as fillers are added, it may also be formulated as a lyophilized dosage form.

The present invention is explained in more detail by means of the following Examples but should not be construed to be limited thereto. In the following Examples, reagents manufactured by Wako Pure Chemical Industries, Ltd., TAKARA SHUZO CO., LTD. or Difco were used unless otherwise mentioned.

EXAMPLE 1

(1) Cloning of Genes Coding for SpaA and ΔSpaA Proteins

*Erysipelothrix rhusiopathiae*, type 1 Fujisawa strain and Koganai strain, and type 2 Tama 96 strain and SE-9 strain, were cultured in Brain Heart Infusion medium (Difco) supplemented with 0.1% Tween 80 at 37° C. for 16 to 48 hours. The culture (about 1.5 to 3.0 mL) was centrifuged. A total genome DNA was extracted from the obtained precipitate (about 0.03 g or more) with a DNA extraction kit (Isoplant, NIPPON GENE CO., LTD.).

With the total genome DNA as a template, PCR was performed using synthetic primers (a pair of SEQ ID NOs: 3 and 4, a pair of SEQ ID NOs: 3 and 5), prepared on the basis of the nucleotide sequence of SEQ ID NO: 1, and LAPCR Kit (TAKARA). The reaction solution was kept at 94° C. for 3 minutes and then a cycle of 94° C. for 60 seconds, 56° C. for 30 seconds and 72° C. for 60 seconds was repeated for 30 cycles. The primer of SEQ ID NO: 3 was designed for amplifying the region downstream from the 79th nucleotide of SpaA gene wherein NcoI site was added at its 5' end. The primers of SEQ ID NOs: 4 and 5 were designed for amplifying the region up to the 1260th and 1881st (termination codon of SpaA gene) nucleotides of SpaA gene, respectively, wherein BamHI site was added at its 5' end. The PCR provides SpaA gene having the nucleotide sequence of from the 79th to 1881st and the SpaA gene having the nucleotide sequence of from the 79th to 1260th.

The DNA fragments amplified by PCR were dually digested with NcoI and BamHI and the resulting digested products were ligated with a plasmid pET11d (Novagen), which has previously been digested dually with NcoI and BamHI, using T4 DNA ligase. This reaction solution was mixed with *E. coli* JM109. The mixture was left to stand in ice for several ten seconds, applied to LB agar (1.0% Tryptone, 0.5% Yeast Extract, 1.0% NaCl, 1.5% agar, pH 7.0) supplemented with ampicillin 50 µg/ml and left to stand at 37° C. overnight. A single colony was inoculated to 1 to 5 mL LB medium supplemented with ampicillin 50 µg/ml and the medium was shook at 30 to 37° C., followed by a routine work-up to extract plasmids containing the gene coding for SpaA and ΔSpaA proteins from the cells (FIGS. 1-*a* and 1-*b*).

(2) Expression of SpaA and ΔSpaA Proteins

Figure 2A:
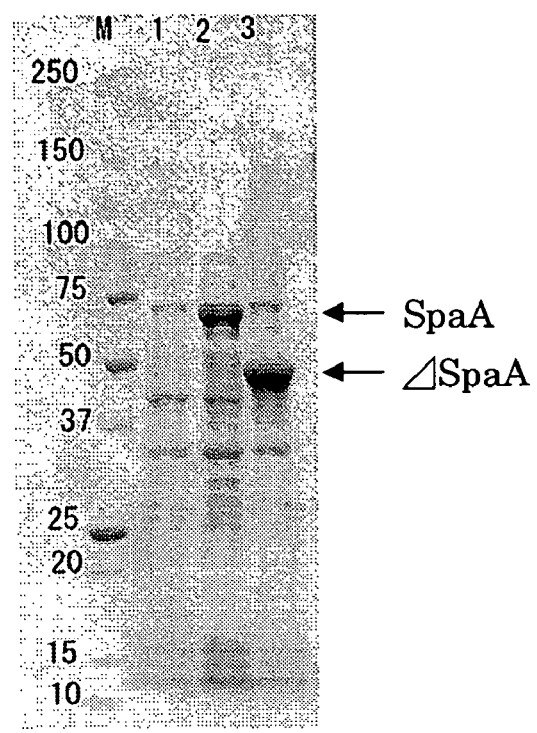
FIG. 2A shows results of SDS-PAGE performed on SpaA protein derived from *Erysipelothrix rhusiopathiae* SE-9 strain and ΔSpaA protein. M: Marker; Lane 1: culture of *E. coli* not expressing a foreign protein; Lane 2: culture of *E. coli* expressing SpaA protein; Lane 3: culture of *E. coli* expressing ΔSpaA protein.
Figure 2B:
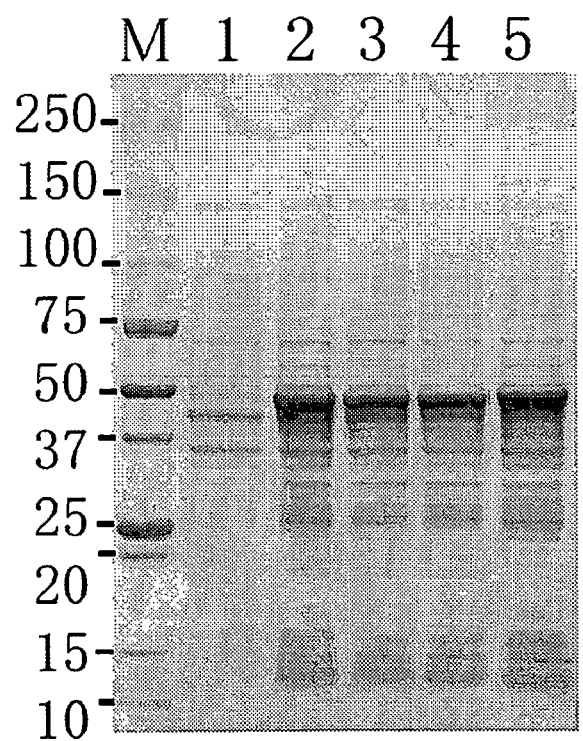
FIG. 2B shows results of SDS-PAGE performed on ΔSpaA protein derived from *Erysipelothrix rhusiopathiae*. M: Marker; Lane 1: culture of *E. coli* not expressing a foreign protein; Lane 2: culture of *E. coli* expressing ΔSpaA protein derived from Fujisawa strain; Lane 3: culture of *E. coli* expressing ΔSpaA protein derived from Tama 96 strain; Lane 4: culture of *E. coli* expressing ΔSpaA protein derived from Koganai strain; Lane 5: culture of *E. coli* expressing ΔSpaA protein derived from SE-9 strain.

As described in Example 1-(1), the plasmids from each of the different strains were introduced into *E. coli* BL21(DE3) to give single colonies of transformant. The single colonies were inoculated to 1 to 5 mL LB medium supplemented with ampicillin 50 µg/ml and cultured while shaking at 30 to 37° C. until OD600 nm of the culture reached 0.6 to 1.0. A 1/100-volume of IPTG (100 mM) was added to the culture and shake-culture further continued at 37° C. for 2 to 3 hours. The culture was mixed with an equivalent volume of 2×SDS sample buffer and, after heating at 100° C. for 2 minutes, the mixture was applied to SDS-polyacrylamide gel electrophoresis (SDS-PAGE) and stained with Coomassie Brilliant Blue (nacalai tesque). For all the strains, bands at around 70 and 45 kD were detected, from which stained image expression of SpaA and ΔSpaA proteins was confirmed. FIG. 2A shows results of SDS-PAGE for SpaA and ΔSpaA proteins derived from SE-9 strain; FIG. 2B shows results of SDS-PAGE for SpaA and ΔSpaA proteins derived from Fujisawa strain, Tama 96 strain, Koganai strain and SE-9 strain.

(3) Form of SpaA and ΔSpaA Proteins

Figure 3:
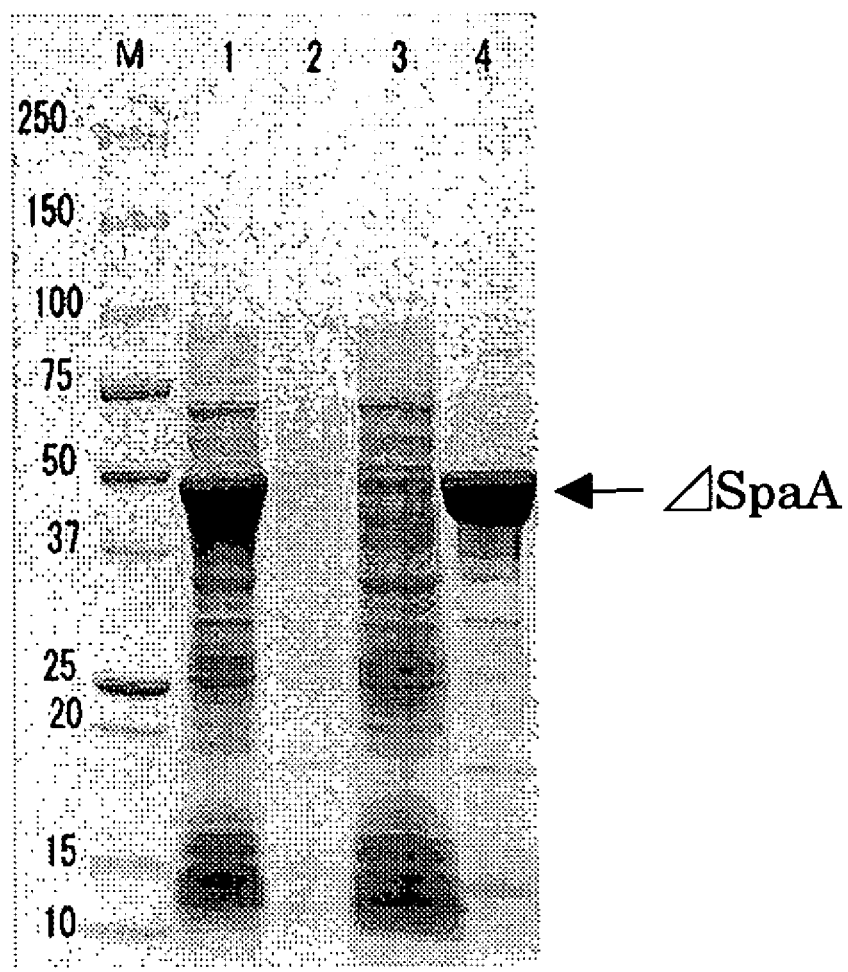
FIG. 3 shows results of SDS-PAGE performed on soluble and insoluble (inclusion bodies) ΔSpaA proteins derived from *Erysipelothrix rhusiopathiae* SE-9 strain. M: Marker; Lane 1: supernatant of centrifugation of sonicated culture of *E. coli* expressing soluble ΔSpaA protein; Lane 2: precipitates of centrifugation of sonicated culture of *E. coli* expressing soluble ΔSpaA protein; Lane 3: supernatant of centrifuge of sonicated culture of *E. coli* expressing insoluble ΔSpaA protein; Lane 4: precipitates of centrifugation of sonicated culture of *E. coli* expressing insoluble ΔSpaA protein.

Whether inclusion bodies of SpaA and ΔSpaA proteins were formed was investigated as described below. The culture of Example 1-(2) was centrifuged at 10,000 rpm for 5 minutes and the resulting precipitate was added with a 1/5 to 1/10 volume, based on the culture, of a washing buffer (20 mM Tris-HCl pH 7.5, 10 mM EDTA, 1% Triton X-100) or distilled water and the cells were suspended to uniformity. To the suspension was added a 1/100 volume of a lysozyme solution (10 mg/ml) for reaction at 30° C. for 15 minutes. The mixture under ice-cooling was sonicated with a handy sonicater (manufacturer: Tomy; Model: UR-20P; Output: 5; Time: 15 seconds, 2 to 4 times) and centrifuged at 15,000 rpm for 15 minutes. After supernatant was collected, the precipitate was added with an equivalent volume, based on the sonicated mixture before centrifugation, of a washing buffer and the cells were again suspended to uniformity. To each of the collected supernatant and the precipitate was added an equivalent volume of 2×SDS sample buffer. After heating, each of the mixture was applied to SDS-PAGE and stained with Coomassie Brilliant Blue. If ΔSpaA protein was found in the suspension of precipitate, said ΔSpaA protein was assessed to form inclusion bodies (FIG. 3). As a result, formation of inclusion bodies was detected in several clones of SE-9 strain (Table 1). Table 1 shows the number of clones that formed inclusion bodies out of the number of clones investigated. ND means "not done".

TABLE 1

|  | Clones forming inclusion bodies/Clones expressing ΔSpaA | Clones forming inclusion bodies/Clones expressing SpaA |
| --- | --- | --- |
| Fujisawa strain (type 1) | 0/3 | ND |
| SE-9 strain (type 2) | 3/30 | 1/15 |
| Tama 96 strain (type 2) | 0/3 | ND |
| Koganai strain (type 1) | 0/3 | ND |

(4) Nucleotide Sequence Determination in Clones Forming Inclusion Bodies

Next, plasmids were extracted from the four clones of SE-9 strain in Table 1 which formed inclusion bodies (No. 1, No. 2, No. 3 and No. 4) and nucleotide sequence of the gene coding for ΔSpaA protein was analyzed by entrusting TAKARA BIO INC., custom service center. On comparison with the sequence of SEQ ID NO: 7, the amino acid substitutions due to nucleotide mutations as depicted in Table 2 were observed.

TABLE 2

| Nucl. position | Nucleotide substitution (corresponding amino acid substitution) | Clone |
| --- | --- | --- |
| 206th | A to G (the 69th glutamic acid to glycine) | No. 2 |
| 461st | A to G (the 154th glutamic acid to glycine) | No. 2 |
| 608th | T to C (the 203rd isoleucine to threonine) | No. 2 |
| 642nd | T to G (the 214th histidine to glutamine) | No. 1 |
| 758th | T to C (the 253rd methionine to threonine) | No. 1 |
| 833rd | A to G (the 278th aspartic acid to glycine) | No. 3 |
| 1591st | A to G (the 531st arginine to glycine) | No. 4 |

EXAMPLE 2

(1) Protein Expression as Inclusion Bodies by Amino Acid Substitution of ΔSpaA Protein Plasmids were constructed wherein DNA fragments with the nucleotide substitutions as depicted in Table 2 produced by cleaving the plasmids from the clones forming inclusion bodies in Example 1-(4) with suitable restriction enzymes were replaced for the corresponding region in the gene coding for ΔSpaA protein in the plasmids extracted from the clones (SE-9 strain) expressing soluble ΔSpaA protein.

Figure 4A:
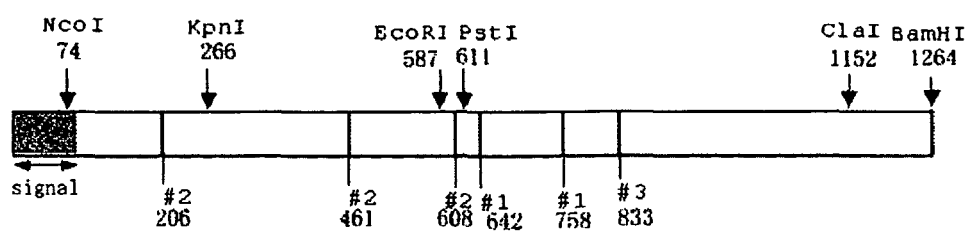
FIG. 4A shows mutated sites and restriction enzyme cleavage sites found in SpaA gene in the plasmids extracted from *E. coli* transformant cells (three clones; No. 1, No. 2 and No. 3) expressing insoluble (inclusion bodies) ΔSpaA protein from comparison with SEQ ID NO: 7.
Figure 4A:
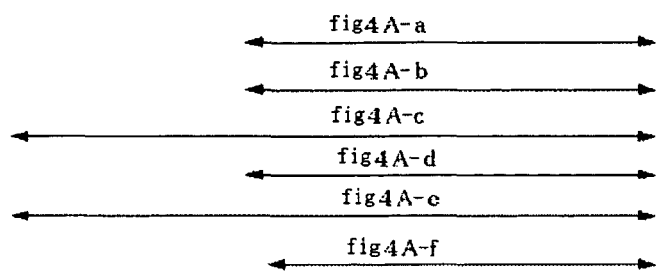

Specifically, (a) the plasmid from the clone No. 1, after dual digestion with the restriction enzymes EcoRI and ClaI, was applied to agarose electrophoresis to isolate and separate an EcoRI-ClaI fragment which comprised the gene coding for ΔSpaA protein ranging from the 587th to 1152nd nucleotides (FIG. 4A-1). The obtained fragment was inserted into the plasmid from the clones (SE-9 strain) expressing soluble ΔSpaA protein previously treated with EcoRI and ClaI to thereby prepare a plasmid comprising the gene coding for ΔSpaA protein in which the 642nd and 758th nucleotides were substituted.

Figure 4B:
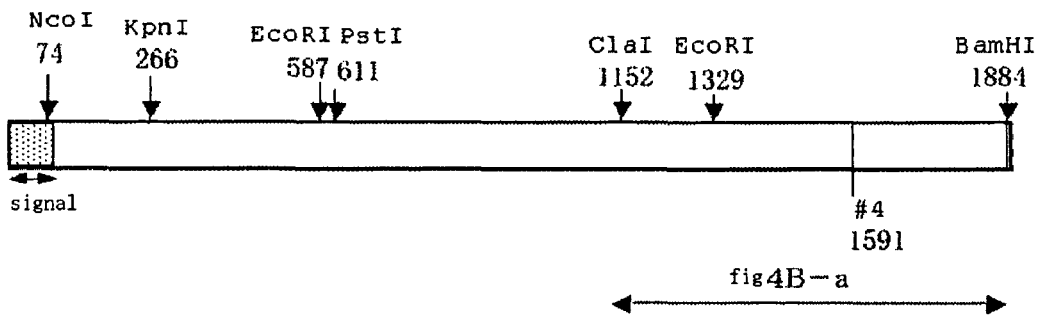
FIG. 4B shows mutated sites and restriction enzyme cleavage sites found in SpaA gene in the plasmid extracted from *E. coli* transformant cells (one clone; No. 4) expressing insoluble (inclusion bodies) SpaA protein from comparison with SEQ ID NO: 7.

In the same manner, (b) a plasmid wherein an EcoRI-ClaI fragment which comprised the gene coding for ΔSpaA protein ranging from the 587th to 1152nd nucleotides (FIG. 4A-b) from the clone No. 3 was inserted (substitution at the 833rd nucleotide);

(c) a plasmid wherein a KpnI-ClaI fragment which comprised the gene coding for ΔSpaA protein ranging from the 266th to 1152nd nucleotides (FIG. 4A-c) from the clone No. 2 was inserted (substitutions at the 461st and 608th nucleotides); and (d) a plasmid wherein an EcoRI-ClaI fragment which comprised the gene coding for ΔSpaA protein ranging from the 587th to 1152nd nucleotides (FIG. 4A-d) from the clone No. 2 was inserted (substitution at the 608th nucleotide) were constructed.

(e) A plasmid comprising the gene coding for ΔSpaA protein in which the 206th nucleotide was substituted was constructed by inserting a KpnI-ClaI fragment which comprises the gene coding for soluble ΔSpaA protein ranging from the 266th to 1152nd nucleotides (FIG. 4A-e) into the plasmid from the clone No. 2 treated with KpnI and ClaI.

(f) A plasmid comprising the gene coding for ΔSpaA protein in which the 642nd nucleotide was substituted was constructed by site-directed mutagenesis (Takara, Mutan-Super Express Km). Specifically, the plasmid (FIG. 1-b) from the clones (SE-9 strain) expressing soluble ΔSpaA protein was dually digested with EcoRI and HindIII and the resulting EcoRI-HindIII fragment (967 bp), which comprised the gene coding for ΔSpaA protein ranging from the 587th to 1260th nucleotides and a portion of the plasmid pET11d, was cloned into a vector plasmid pKF18k (Takara) Using this plasmid as a template, PCR was performed as described in Example 1-(1) with the synthetic oligonucleotide for mutagenesis of SEQ ID NO: 6, comprising a sequence of from the 632nd to 657th nucleotides of the gene coding for ΔSpaA protein in which the 642nd nucleotide T was substituted with G, 5 μmol of selection primers attached to Mutan-Super Express Km Kit from Takara, 5 μl of 10×LAPCR buffer (+Mg$^{2+}$), 8 μl of a mixture of dNTPs, 0.5 μl of an LA-Taq polymerase solution and sterilized distilled water to make a total volume of 50 μl. The resulting PCR solution, after ethanol precipitation/washing, was cloned into E. coli MV1184 strain (Takara). The obtained plasmid with the mutagenesis was dually digested with EcoRI and BamHI to separate and isolate an EcoRI-BamHI fragment comprising the gene coding for ΔSpaA protein ranging from the 587th to 1260th nucleotides. This fragment was inserted into the corresponding region of the plasmid from the clones (SE-9 strain) expressing soluble ΔSpaA protein, a starting material, to give a desired plasmid. Likewise, a plasmid comprising the gene coding for ΔSpaA protein in which the 642nd nucleotide T was substituted by G was constructed for Fujisawa strain and Tama 96 strain with the same procedure.

The thus obtained plasmids were used for transformation of E. coli BL21(DE3) and the form of the expressed ΔSpaA proteins was surveyed. As a result, it was found that every ΔSpaA protein from the transformants with any of the plasmids formed inclusion bodies.

(2) Protein Expression as Inclusion Bodies by Amino Acid Substitution of Full-Length SpaA Protein Plasmids were constructed wherein DNA fragments with the nucleotide substitutions as depicted in Table 2 produced by cleaving the plasmids from the clones forming inclusion bodies in Example 1-(4) with suitable restriction enzymes were replaced for the corresponding region in the gene coding for SpaA protein in the plasmids extracted from the clones (SE-9 strain) expressing soluble SpaA protein.

Specifically, (a) the plasmid from the clone No. 4, after dual digestion with the restriction enzymes ClaI and BamHI, was applied to agarose electrophoresis to isolate and separate a ClaI-BamHI fragment (FIG. 4B-a) which comprised a sequence of from the 1152nd to 1881st nucleotides (termination codon of the gene coding for SpaA protein) of the gene coding for SpaA protein. The obtained fragment was inserted into the plasmid from the clones (SE-9 strain) expressing soluble full-length SpaA protein previously treated with ClaI and BamHI to thereby prepare a plasmid comprising the gene coding for SpaA protein in which the 1591st nucleotide was substituted.

(b) the plasmid obtained in Example 2-(1)-(a), after dual digestion with PstI and ClaI, was applied to agarose electrophoresis to isolate and separate a PstI-ClaI fragment (FIG. 4A-f) which comprised a sequence of from the 611th to 1152nd nucleotides of the gene coding for ΔSpaA protein. The obtained fragment was inserted into the plasmid from the clones (SE-9 strain) expressing soluble full-length SpaA protein previously treated with PstI and ClaI to thereby prepare a plasmid comprising the gene coding for SpaA protein in which the 642nd and 758th nucleotides were substituted.

Figure 5:
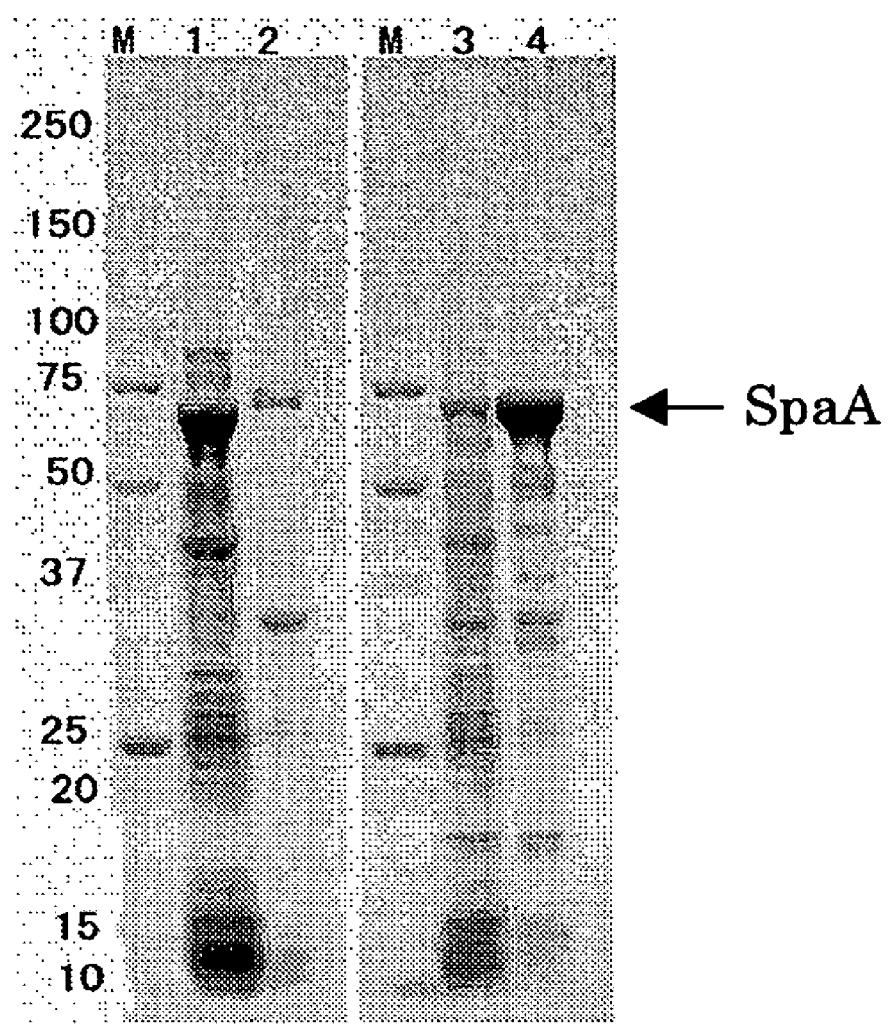
FIG. 5 shows results of SDS-PAGE performed on soluble and insoluble (inclusion bodies) SpaA proteins derived from *Erysipelothrix rhusiopathiae* SE-9 strain. M: Marker; Lane 1: supernatant of centrifugation of sonicated culture of *E. coli* expressing soluble SpaA protein; Lane 2: precipitates of centrifugation of sonicated culture of *E. coli* expressing soluble SpaA protein; Lane 3: supernatant of centrifugation of sonicated culture of *E. coli* expressing insoluble SpaA protein; Lane 4: precipitates of centrifugation of sonicated culture of *E. coli* expressing insoluble SpaA protein.

The thus obtained plasmids were used for transformation of E. coli BL21(DE3) and the form of the expressed SpaA proteins was surveyed. As a result, it was found that every SpaA protein from the transformants with any of the plasmids formed inclusion bodies (FIG. 5).

EXAMPLE 3

(1) Purification of SpaA or ΔSpaA Protein Forming Inclusion Bodies

Figure 6:
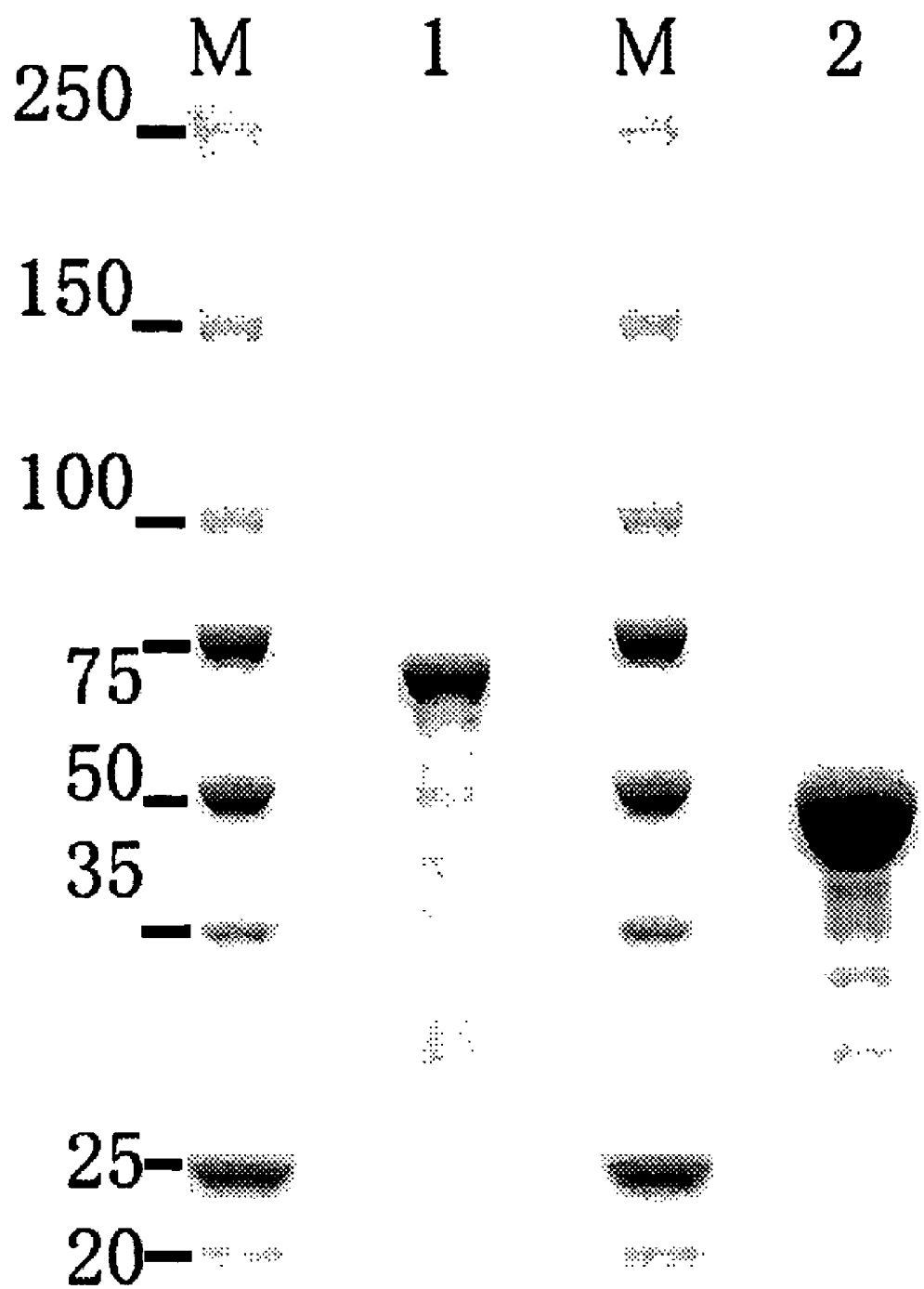
FIG. 6 shows results of SDS-PAGE performed on insoluble (inclusion bodies) SpaA and ΔSpaA proteins derived from *Erysipelothrix rhusiopathiae* SE-9 strain after purification. M: Marker; Lane 1: SpaA protein; Lane 2: ΔSpaA protein.

Each of the E. coli cells expressing ΔSpaA protein as inclusion bodies obtained in Example 2-(1) and the E. coli cells expressing full-length SpaA protein as inclusion bodies obtained in Example 2-(2) were cultured. Each 100 ml of the cultures was centrifuged at 10,000 rpm for 5 minutes and the resulting precipitate was added with a ⅕ to 1/10 volume, based on the culture, of a washing buffer (20 mM Tris-HCl pH 7.5, 10 nM EDTA, 1% Triton X-100) and the cells were suspended to uniformity. To the suspension was added a 1/100 volume of a lysozyme solution (10 mg/ml) for reaction at 30° C. for 15 minutes. The mixture under ice-cooling was sonicated with a sound beam type cell homogenizer (manufacturer: Branson Sonic Power Co.; Model: 350; Output: 4; Duty Cycle; 30%; Time: 5 to 15 minutes) and centrifuged at 15,000 rpm for 15 minutes. After supernatant was collected, the precipitate was added with an equivalent volume, based on the sonicated mixture before centrifugation, of a washing buffer (or sterilized distilled water) and the cells were again suspended to uniformity. The suspension was centrifuged at 15,000 rpm for 15 minutes. After supernatant was collected, the precipitate was added with a washing buffer (or sterilized distilled water). This procedure of centrifugation/washing was repeated three to five times. For the final washing procedure, the precipitate after centrifugation was suspended in sterilized distilled water. The suspension was again centrifuged at 15,000 rpm for 15 minutes. After supernatant was collected, the precipitate was suspended in 10 ml of 8 M urea. While gently shaking at room temperature for 2 hours and then at 5° C. for 18 hours, the protein of inclusion bodies was solubilized to give purified SpaA or ΔSpaA protein. The gel after SDS-PAGE was stained with Coomassie Brilliant Blue. Determination with a densitometer demonstrated that SpaA and ΔSpaA proteins thus obtained had 90% or more purity (FIG. 6).

(2) Immunogenicity of SpaA or ΔSpaA Protein

Immunogenicity of SpaA or ΔSpaA protein was determined as described below. To 4 ml of a solution of SpaA or ΔSpaA protein purified in Example 3-(1) were added 11 ml of saline and 5 ml of aluminum hydroxide gel adjuvant (ALHYDROGEL "85", Superfos Biosector) and the mixture was stirred at room temperature for 2 hours to give a vaccine solution. This vaccine solution was serially diluted by 5-fold in saline supplemented with 25% (vol/vol) aluminum hydroxide gel to prepare serial dilution which was used for immunization of 10 mice (ddy, 5 weeks old, female) per dilution by subcutaneous administration of 0.5 ml. Three weeks after immunization, mice were challenged by intradermal injection of about 1,000 bacterial live cells of Fujisawa strain, a virulent strain of Erysipelothrix rhusiopathiae. Survival or death of mice was observed for 10 days and a median protective dose (PD50) of purified SpaA or ΔSpaA protein was determined. As shown in Table 3, purified SpaA or ΔSpaA protein exhibited extremely high immunogenicity, i.e. a median protective dose (PD50) of 0.0621 to 0.1885 μg. A median protective dose (50% effective dose) in mice was calculated by Behrens-Karber method as described in Karber G: Beitrag zur kollektiven Behandlung pharmakologischer Reihenversuche. Arch. Exp. Path. Pharm., 162:480, 1931; "Saikingaku Jisshu Teiyo" [Summary Practice in Bacteriology], 5th ed., Ed. by "alumni association of Ikagakukenkyusho" [Medical Science Laboratory], Maruzen, p. 564-565, and in accordance with the following equation:

Median protective dose in mice (μg)=$10^m$, $m = X_4 - [(h_0+h_1)(X_1-X_0) \times \frac{1}{2} + (h_1+h_2)(X_2-X_1) \times \frac{1}{2} + (h_2+h_3)(X_3-X_2) \times \frac{1}{2} + (h_4+h_3)(X_4-X_3) \times \frac{1}{2}]$ wherein each of $X_0, X_1, \ldots X_4$ represents logarithm of the respective doses, and each of $h_0, h_1, \ldots h_4$ represents corresponding effective rate (number of survival/number of challenged) by actual measurement. Logarithm (X) of the respective doses may be given by the equation: X=Log 10[protein concentration of a sample (μg/ml)×dose in mice (ml)÷fold of dilution]

TABLE 3

| Purified protein | ΔSpaA | | | SpaA | |
|---|---|---|---|---|---|
| Site of subst. in SpaA gene | 642nd 758th | 206th 461st 608th | 833rd | 1591st | 642nd 758th |
| Protein conc. (mg/ml) | 2.30 | 1.91 | 2.33 | 2.11 | 2.28 |
| Fold of dilution | No. of survival/ No. of challenged | No. of survival/ No. of challenged | No. of survival/ No. of challenged | No. of survival/ No. of challenged | No. of survival/ No. of challenged |
| 625 | 10/10 | 10/10 | 10/10 | 10/10 | 10/10 |
| 3125 | 9/10 | 8/10 | 10/10 | 10/10 | 10/10 |
| 15625 | 5/10 | 0/10 | 4/10 | 4/10 | 6/10 |
| 78125 | 0/10 | 0/10 | 0/10 | 0/10 | 0/10 |
| Median protective dose in mice (μg) | 0.0864 | 0.1885 | 0.0875 | 0.0793 | 0.0621 |

INDUSTRIAL APPLICABILITY

In accordance with the present invention, a process for preparing a soluble SpaA or ΔSpaA protein in *E. coli* as insoluble inclusion bodies is provided. Application of the process of the present invention to a process for preparation of a soluble protein allows for establishment of a process for preparing SpaA or ΔSpaA protein at a practical level, which ensures stable provision of SpaA or ΔSpaA protein in the commercial market. A recombinant SpaA or ΔSpaA protein obtained by the process of the present invention retains immunogenicity equivalent to that of the original soluble protein and may be used as materials for preparing a vaccine to *Erysipelothrix rhusiopathiae* infection alone or in admixture with various additives such as a stabilizing agent, a protective agent, a preserving agent, and the like. It may also be used as an antigen for preparing a monoclonal/polyclonal antibody or as research materials for investigating binding between anti-SpaA or anti-ΔSpaA antibody and *Erysipelothrix rhusiopathiae*. As such, SpaA or ΔSpaA protein obtained by the process of the present invention would greatly contribute to the medical and research field.

The invention claimed is:

1. An isolated variant of an *Erysipelothrix rhusiopathiae* surface protective antigen SpaA protein or of a shortened form thereof (known as ΔSpaA protein),
   wherein the SpaA protein comprises the amino acid sequence encoded by the nucleotide sequence of SEQ ID NO:7, and the ΔSpaA protein is a shortened form of the SpaA protein in which the C-terminal 206 amino acid residues of the SpaA protein comprising the amino acid sequence encoded by the nucleotide sequence of SEQ ID NO:7 are deleted,
   wherein said variant is immunogenic, and expressed in *E. coli* as inclusion bodies, and is selected from the group consisting of:
   (1) the SpaA protein comprising the amino acid sequence encoded by SEQ ID NO:7 with the amino acid substitution of arginine to glycine at the residue corresponding to residue position 531 of SEQ ID NO:2;
   (2) the SpaA protein comprising the amino acid sequence encoded by SEQ ID NO:7 with the amino acid substitution of histidine to glutamine at the residue corresponding to residue position 214 of SEQ ID NO:2 and the amino acid substitution of methionine to threonine at the residue corresponding to residue position 253 of SEQ ID NO:2;
   (3) the ΔSpaA protein with the amino acid substitution of histidine to glutamine at the residue corresponding to residue position 214 of SEQ ID NO:2 and the amino acid substitution of methionine to threonine at the residue corresponding to residue position 253 of SEQ ID NO:2;
   (4) the ΔSpaA protein with the amino acid substitution of glutamic acid to glycine at the residue corresponding to residue position 69 of SEQ ID NO:2, the amino acid substitution of glutamic acid to glycine at the residue corresponding to residue position 154 of SEQ ID NO:2, and the amino acid substitution of isoleucine to threonine at the residue corresponding to residue position 203 of SEQ ID NO:2; and
   (5) the ΔSpaA protein with the amino acid substitution of aspartic acid to glycine at the residue corresponding to residue position 278 of SEQ ID NO:2.

2. A composition comprising as an active ingredient an isolated variant of an *Erysipelothrix rhusiopathiae* surface protective antigen SpaA protein or of a shortened form thereof (known as ΔSpaA protein),
   wherein the SpaA protein comprises the amino acid sequence encoded by the nucleotide sequence of SEQ ID NO:7, and the ΔSpaA protein is a shortened form of the SpaA protein, in which the C-terminal 206 amino acid residues of the SpaA protein comprising the amino acid sequence encoded by the nucleotide sequence of SEQ ID NO:7 are deleted,
   wherein said variant is immunogenic, and expressed in *E. coli* as inclusion bodies, and is selected from the group consisting of:
   (1) the SpaA protein comprising the amino acid sequence encoded by SEQ ID NO:7 with the amino acid substitution of arginine to glycine at the residue corresponding to residue position 531 of SEQ ID NO:2;
   (2) the SpaA protein comprising the amino acid sequence encoded by SEQ ID NO:7 with the amino acid substitution of histidine to glutamine at the residue corresponding to residue position 214 of SEQ ID NO:2 and the amino acid substitution of methionine to threonine at the residue corresponding to residue position 253 of SEQ ID NO:2;
   (3) the ΔSpaA protein with the amino acid substitution of histidine to glutamine at the residue corresponding to residue position 214 of SEQ ID NO:2 and the amino acid substitution of methionine to threonine at the residue corresponding to residue position 253 of SEQ ID NO:2;
   (4) the ΔSpaA protein with the amino acid substitution of glutamic acid to glycine at the residue corresponding to residue position 69 of SEQ ID NO:2, the amino acid substitution of glutamic acid to glycine at the residue corresponding to residue position 154 of SEQ ID NO:2, and the amino acid substitution of isoleucine to threonine at the residue corresponding to residue position 203 of SEQ ID NO:2; and
   (5) the ΔSpaA protein with the amino acid substitution of aspartic acid to glycine at the residue corresponding to residue position 278 of SEQ ID NO:2.

3. A method for immunizing against infection with *Erysipelothrix rhusiopathiae*, comprising administering the variant of claim 1 to an animal in need of immunization.

4. The isolated variant of claim 1, wherein the SpaA protein comprises the amino acid sequence encoded by SEQ ID NO:7 with the amino acid substitution of arginine to glycine at the residue corresponding to residue position 531 of SEQ ID NO:2.

5. The isolated variant of claim 1, wherein the SpaA protein comprises the amino acid sequence encoded by SEQ ID NO:7 with the amino acid substitution of histidine to glutamine at the residue corresponding to residue position 214 of SEQ ID NO:2 and the amino acid substitution of methionine to threonine at the residue corresponding to residue position 253 of SEQ ID NO:2.

6. The isolated variant of claim 1, which is the ΔSpaA protein with the amino acid substitution of histidine to glutamine at the residue corresponding to residue position 214 of SEQ ID NO:2 and the amino acid substitution of methionine to threonine at the residue corresponding to residue position 253 of SEQ ID NO:2.

7. The isolated variant of claim 1, which is the ΔSpaA protein with the amino acid substitution of glutamic acid to glycine at the residue corresponding to residue position 69 of SEQ ID NO:2, the amino acid substitution of glutamic acid to glycine at the residue corresponding to residue position 154 of SEQ ID NO:2, and the amino acid substitution of isoleucine to threonine at the residue corresponding to residue position 203 of SEQ ID NO:2.

8. The isolated variant of claim 1, which is the ΔSpaA protein with the amino acid substitution of aspartic acid to glycine at the residue corresponding to residue position 278 of SEQ ID NO:2.

9. The composition of claim 2, wherein the SpaA protein comprises the amino acid sequence encoded by SEQ ID NO:7 with the amino acid substitution of arginine to glycine at the residue corresponding to residue position 531 of SEQ ID NO:2.

10. The composition of claim 2, wherein the SpaA protein comprises the amino acid sequence encoded by SEQ ID NO:7 with the amino acid substitution of histidine to glutamine at the residue corresponding to residue position 214 of SEQ ID NO:2 and the amino acid substitution of methionine to threonine at the residue corresponding to residue position 253 of SEQ ID NO:2.

11. The composition of claim 2, which is the ΔSpaA protein with the amino acid substitution of histidine to glutamine at the residue corresponding to residue position 214 of SEQ ID NO:2 and the amino acid substitution of methionine to threonine at the residue corresponding to residue position 253 of SEQ ID NO:2.

12. The composition of claim 2, which is the ΔSpaA protein with the amino acid substitution of glutamic acid to glycine at the residue corresponding to residue position 69 of SEQ ID NO:2, the amino acid substitution of glutamic acid to glycine at the residue corresponding to residue position 154 of SEQ ID NO:2, and the amino acid substitution of isoleucine to threonine at the residue corresponding to residue position 203 of SEQ ID NO:2.

13. The composition of claim 2, which is the ΔSpaA protein with the amino acid substitution of aspartic acid to glycine at the residue corresponding to residue position 278 of SEQ ID NO:2.

* * * * *

SEQUENCE LISTING

<160> NUMBER OF SEQ ID NOS: 7

<210> SEQ ID NO 1
<211> LENGTH: 1881
<212> TYPE: DNA
<213> ORGANISM: Erysipelothrix rhusiopathiae

<400> SEQUENCE: 1

```
atgaaaaaga aaaacacct atttccgaaa gtaagtctta tgtcgtgctt acttttaaca      60
gcaatgccac tacaaacagc ttttgctgat tcgacagata tttctgtgat tccactaatc     120
ggtgaacaag ttggattgct cccagttta cctgggacag gggtacatgc tcaggaatac     180
aacaaaatga ctgatgctta tattgaaaaa ttggtatctc taattaatca aaagtgaag     240
ccgtttctta taaatgagcc aaaggggtac caaagtttcg aagcagtgaa tgaagagatt     300
aactcgattg taagtgaact taaaaatgaa ggaatgagtc ttcaaaacat tcaccatatg     360
tttaaacaaa gcatccaaaa cctagcaact agaatcggct acagaagttt tatgcaggat     420
gctatgtatc ttgaaaattt tgaaagatta acgattcctg aacttgatga agcatacgtt     480
gatttactcg tgaattacga ggtgaaacac cgtattttag taaaatatga aggtaaagtt     540
aaaggtagag ctcccttaga agcatttata gttcctctaa gagatagaat tcgtagtatg     600
aatgaaattg ctgcagaagt aaattattta cctgaagcgc atgaggattt cttagtttca     660
gattcaagcg agtataatga caaactaaat aatatcaact ttgctttggg tctagggtc     720
agcgagttta ttgactataa ccggctcgaa aatatgatgg aaaaagaact tcatccactg     780
tatcttgaac tttatgctat gcggagaaat cgccaaattc aagttgtaag agatgtatat     840
ccaaacttgg aacgtgcgaa cgcggttgtt gaatccttaa agacaattaa agatataaaa     900
caagaggga agaaactaca ggaacttctt gaaatttata tccaaagaag tggagatgtt     960
cgaaaaccag atgtactcca acgatttatt ggaaaatatc aatcagtagt tgatgaagaa    1020
aaaaataaac ttcaagatta tttagaatca gatattttg attcatatag tgtggatggc    1080
gagaaaataa gaaataaaga aattacactc atcaatagag atgcatactt atctatgatt    1140
tacagagctc aatcgatttc ggaaattaag acgattcgtg cagatttaga atcacttgtc    1200
aaatcattcc aaaatgaaga aagtgactct aaagtagagc ctgaaagtcc cgttaaagta    1260
gaaaaaccag ttgatgaaga aaaacctaaa gatcaaaaga agctagttga tcaatcaaaa    1320
cccgaatcga attcaaaaga agggtggatt aagaaagata ataagtggtt ctatattgag    1380
aaatcaggtg aatggcaac aggttggaag aaggtagcag acaaatggta ctacctcgat    1440
aatacgggtg ctatagttac gggttggaag aaggtagcaa acaaatggta ctatcttgaa    1500
aaatcaggtg cgatggcaac aggatggaag aaagtatcaa acaagtggta ctaccttgaa    1560
aactcaggtg caatggcaac aggatggaag aaagtatcaa acaagtggta ctaccttgaa    1620
```

-continued

```
aattcaggcg caatggctac aggatggaaa aaggtagcaa acaaatggta ctaccttgaa   1680
aactcaggtg cgatggcaac aggatggaag aaagtatcga acaagtggta ctaccttgaa   1740
aactcaggcg caatggctac aggatggaaa aaggtagcaa acaaatggta ctaccttgat   1800
aaatcaggaa tgatggttac aggttcaaaa tctattgatg gtaaaaagta tgcatttaag   1860
aacgatggaa gtttaaaata g                                             1881

<210> SEQ ID NO 2
<211> LENGTH: 626
<212> TYPE: PRT
<213> ORGANISM: Erysipelothrix rhusiopathiae

<400> SEQUENCE: 2

Met Lys Lys Lys Lys His Leu Phe Pro Lys Val Ser Leu Met Ser Cys
1               5                   10                  15

Leu Leu Leu Thr Ala Met Pro Leu Gln Thr Ala Phe Ala Asp Ser Thr
            20                  25                  30

Asp Ile Ser Val Ile Pro Leu Ile Gly Glu Gln Val Gly Leu Leu Pro
        35                  40                  45

Val Leu Pro Gly Thr Gly Val His Ala Gln Glu Tyr Asn Lys Met Thr
    50                  55                  60

Asp Ala Tyr Ile Glu Lys Leu Val Ser Leu Ile Asn Gln Lys Val Lys
65                  70                  75                  80

Pro Phe Leu Ile Asn Glu Pro Lys Gly Tyr Gln Ser Phe Glu Ala Val
                85                  90                  95

Asn Glu Glu Ile Asn Ser Ile Val Ser Glu Leu Lys Asn Glu Gly Met
            100                 105                 110

Ser Leu Gln Asn Ile His His Met Phe Lys Gln Ser Ile Gln Asn Leu
        115                 120                 125

Ala Thr Arg Ile Gly Tyr Arg Ser Phe Met Gln Asp Ala Met Tyr Leu
    130                 135                 140

Glu Asn Phe Glu Arg Leu Thr Ile Pro Glu Leu Asp Glu Ala Tyr Val
145                 150                 155                 160

Asp Leu Leu Val Asn Tyr Glu Val Lys His Arg Ile Leu Val Lys Tyr
                165                 170                 175

Glu Gly Lys Val Lys Gly Arg Ala Pro Leu Glu Ala Phe Ile Val Pro
            180                 185                 190

Leu Arg Asp Arg Ile Arg Ser Met Asn Glu Ile Ala Ala Glu Val Asn
        195                 200                 205

Tyr Leu Pro Glu Ala His Glu Asp Phe Leu Val Ser Asp Ser Ser Glu
    210                 215                 220

Tyr Asn Asp Lys Leu Asn Asn Ile Asn Phe Ala Leu Gly Leu Gly Val
225                 230                 235                 240

Ser Glu Phe Ile Asp Tyr Asn Arg Leu Glu Asn Met Met Glu Lys Glu
                245                 250                 255

Leu His Pro Leu Tyr Leu Glu Leu Tyr Ala Met Arg Arg Asn Arg Gln
            260                 265                 270

Ile Gln Val Val Arg Asp Val Tyr Pro Asn Leu Glu Arg Ala Asn Ala
        275                 280                 285

Val Val Glu Ser Leu Lys Thr Ile Lys Asp Ile Lys Gln Arg Gly Lys
    290                 295                 300

Lys Leu Gln Glu Leu Leu Glu Ile Tyr Ile Gln Arg Ser Gly Asp Val
305                 310                 315                 320

Arg Lys Pro Asp Val Leu Gln Arg Phe Ile Gly Lys Tyr Gln Ser Val
```

```
                    325                 330                 335
Val Asp Glu Glu Lys Asn Lys Leu Gln Asp Tyr Leu Glu Ser Asp Ile
                340                 345                 350

Phe Asp Ser Tyr Ser Val Asp Gly Glu Lys Ile Arg Asn Lys Glu Ile
                355                 360                 365

Thr Leu Ile Asn Arg Asp Ala Tyr Leu Ser Met Ile Tyr Arg Ala Gln
            370                 375                 380

Ser Ile Ser Glu Ile Lys Thr Ile Arg Ala Asp Leu Gly Ser Leu Val
385                 390                 395                 400

Lys Ser Phe Gln Asn Glu Glu Ser Asp Ser Lys Val Glu Pro Glu Ser
                405                 410                 415

Pro Val Lys Val Glu Lys Pro Val Asp Glu Glu Lys Pro Lys Asp Gln
                420                 425                 430

Lys Lys Leu Val Asp Gln Ser Lys Pro Glu Ser Asn Ser Lys Glu Gly
            435                 440                 445

Trp Ile Lys Lys Asp Asn Lys Trp Phe Tyr Ile Glu Lys Ser Gly Gly
            450                 455                 460

Met Ala Thr Gly Trp Lys Lys Val Ala Asp Lys Trp Tyr Tyr Leu Asp
465                 470                 475                 480

Asn Thr Gly Ala Ile Val Thr Gly Trp Lys Lys Val Ala Asn Lys Trp
                485                 490                 495

Tyr Tyr Leu Glu Lys Ser Gly Ala Met Ala Thr Gly Trp Lys Lys Val
                500                 505                 510

Ser Asn Lys Trp Tyr Tyr Leu Glu Asn Ser Gly Ala Met Ala Thr Gly
            515                 520                 525

Trp Lys Lys Val Ser Asn Lys Trp Tyr Tyr Leu Glu Asn Ser Gly Ala
530                 535                 540

Met Ala Thr Gly Trp Lys Lys Val Ala Asn Lys Trp Tyr Tyr Leu Glu
545                 550                 555                 560

Asn Ser Gly Ala Met Ala Thr Gly Trp Lys Lys Val Ser Asn Lys Trp
                565                 570                 575

Tyr Tyr Leu Glu Asn Ser Gly Ala Met Ala Thr Gly Trp Lys Lys Val
                580                 585                 590

Ala Asn Lys Trp Tyr Tyr Leu Asp Lys Ser Gly Met Met Val Thr Gly
            595                 600                 605

Ser Lys Ser Ile Asp Gly Lys Lys Tyr Ala Phe Lys Asn Asp Gly Ser
            610                 615                 620

Leu Lys
625

<210> SEQ ID NO 3
<211> LENGTH: 37
<212> TYPE: DNA
<213> ORGANISM: Artificial
<220> FEATURE:
<223> OTHER INFORMATION: Sense primer designed for preparation of SpaA
      and fSpaA protein by PCR amplification

<400> SEQUENCE: 3
catgccatgg ctttcgctga ttcgacagat atttctg                              37

<210> SEQ ID NO 4
<211> LENGTH: 33
<212> TYPE: DNA
<213> ORGANISM: Artificial
<220> FEATURE:
<223> OTHER INFORMATION: Antisense primer designed for preparation of
      fSpaA protein by PCR amplification
```

<400> SEQUENCE: 4
cgcggatcct tatactttaa cgggactttc agg 33

<210> SEQ ID NO 5
<211> LENGTH: 38
<212> TYPE: DNA
<213> ORGANISM: Artificial
<220> FEATURE:
<223> OTHER INFORMATION: Antisense primer designed for preparation of SpaA protein by PCR amplification

<400> SEQUENCE: 5
cgcggatccg tctattttaa acttccatcg ttcttaaa 38

<210> SEQ ID NO 6
<211> LENGTH: 24
<212> TYPE: DNA
<213> ORGANISM: Artificial
<220> FEATURE:
<223> OTHER INFORMATION: Oligonucleotide designed for preparation of pointmutated SpaA protein by site directed mutagenesis

<400> SEQUENCE: 6
ctgaagcgca ggaggatttc ttag 24

<210> SEQ ID NO 7
<211> LENGTH: 1748
<212> TYPE: DNA
<213> ORGANISM: Erysipelothrix rhusiopathiae

<400> SEQUENCE: 7
tgattccact aatcggtgaa caagttggat tgctcccagt tttacctggg acagggatac 60
atgctcagga atacaacaaa atgactgatg cttatattga aaatttggta tctctaatta 120
atcaaaaagt gaagccgttt cttataaatg aaccaaaggg gtaccaaagt ttcgaagcag 180
tgaatgaaga gattaactcg attgtaagtg aacttaaaca tgaaggaatg agtcttcaaa 240
acattcacca tatgtttaaa caaagcatcc aaaacctagc aactagaatc ggctacagaa 300
gttttatgca ggatgctatg tatcttgaaa attttgaaag attaacgatt cctgaacttg 360
atgaagcata cgttgattta ctcgtgaatt acgaggtgaa acaccgtatt ttagtaaaat 420
atgaagataa agttaaaggt agagctccat tagaagcatt tatagttcct ctaagaaata 480
gaattcgtag tatgaatgaa attgctgcag aagtaaatta tttacctgaa gcgcatgagg 540
atttcttagt ttcagattca agcgagtata atgacaaact aaataatatc aactttgctt 600
tgggtctagg ggtcagcgag tttattgact ataaccggct cgaaaatatg atggaaaaag 660
aaattcatcc attgtatctt gaactttatg ctatgcggag aaatcgccaa attcaagttg 720
taagagatgt atatccaaac ttggaacgtg cgaacgcggt tgttgaatcc ttaaagacaa 780
ttaaagatat aaaacaaaga gagaagaaac tacaggaact tcttgaaatt tatatccaaa 840
gaagtggaga tgttcgaaaa ccagatgtac tccaacgatt tattggaaaa tatcaatcag 900
tagttgatga agaaaaaaat aaacttcaag attatttaga atcagatatt tttgattcat 960
atagtgtgga tggcgagaaa ataagaaata aagaaattac actcatcaat agagatgcat 1020
acttatctat gatttacaga gctcaatcga tttcggaaat taagacgatt cgtgcagatt 1080
tagaatcact tgtcaaatca ttccaaaatg aagaaagtga ttctaaagta gagcctgaaa 1140
gtcccgttaa agtagaaaaa ccagttgata aagaaaaacc taaagatcaa aagaagccag 1200
ttgatcaatc aaaacccgaa tcgaattcaa aagaagggtg gattaagaaa gataataagt 1260

```
ggttctatat tgagaaatca ggtggaatgg caacaggatg gaagaaggta ggagacaaat    1320
ggtactacct cgataatacg ggtgctatgg ttacgggttg gaagaaggta gcaaacaaat    1380
ggtactacct tgaaaactca ggtgcgatgg caacaggatg gaagaaagta tcaaacaagt    1440
ggtactacct tgaaaactca ggtgcgatgg caacaggatg gaagagagta tcaaacaagt    1500
ggtactacct tgaaaattca ggcgcaatgg ctacaggatg gaaaaaggta gcaaacaaat    1560
ggtactacct tgaaaactca ggtgcgatgg caacaggatg gaagaaagta tcgaacaagt    1620
ggtactacct tgaaaactca ggcgcaatgg caacgggttg gaagaaaata gcaaataaat    1680
ggtactacct tgataaatca ggaatgatgg ttacaggttc aaaatctatt gatggtaaaa    1740
agtatgca                                                             1748
```